United States Patent [19]

Atkinson et al.

[11] 4,148,903

[45] Apr. 10, 1979

[54] ANTIPSYCHOTIC, ANTISEROTONIN AND ANTIHISTAMINIC PYRROLO[2,1-b][3]BENZAZEPINES

[75] Inventors: Joseph G. Atkinson, Montreal; Clarence S. Rooney, Beaconsfield; Patrice C. Bélanger, Dollard des Ormeaux, all of Canada; David C. Remy, North Wales, Pa.

[73] Assignee: Merck & Co., Inc., Rahway, N.J.

[21] Appl. No.: 819,739

[22] Filed: Jul. 28, 1977

[51] Int. Cl.$^2$ ............... A61K 31/445; C07D 401/04; C07D 401/14

[52] U.S. Cl. .................. 424/267; 260/326.5 S; 260/326.5 SF; 260/326.5 B; 260/244.4

[58] Field of Search .................. 260/293.61; 424/267

[56] References Cited

U.S. PATENT DOCUMENTS

| | | | |
|---|---|---|---|
| 3,014,911 | 12/1961 | Engelhardt | 260/293.62 |
| 3,458,522 | 7/1969 | Galantay | 260/293.57 |
| 4,031,222 | 6/1977 | Remy | 260/293.62 |
| 4,056,536 | 11/1977 | Atkinson et al. | 260/326.5 B |

FOREIGN PATENT DOCUMENTS

746508  11/1966  Canada .......................... 260/293.62

OTHER PUBLICATIONS

Gordon, M. *Psychopharmacological Agents*, vol. I, Academic Press, New York, 1964, p. 600.

*Primary Examiner*—Natalie Trousof
*Assistant Examiner*—Richard A. Schwartz
*Attorney, Agent, or Firm*—William H. Nicholson; Harry E. Westlake, Jr.

[57] ABSTRACT

Pyrrolo[2,1-b][3]benzazepines with a piperidinylidene group in the 11-position have utility as antipsychotic agents. They also demonstrate antiserotonin and antihistaminic activity. They are prepared by reaction of a pyrrolo[2,1-b][3]benzazepin-11-one with a piperidinyl magnesium halide followed by dehydration.

12 Claims, No Drawings

ANTIPSYCHOTIC, ANTISEROTONIN AND ANTIHISTAMINIC PYRROLO[2,1-b][3]BENZAZEPINES

BACKGROUND OF THE INVENTION

This invention is concerned with novel pyrrolo-[2,1-b] [3]benzazepines with a piperidinylidene group in the 11-position which are active as antipsychotic, antiserotonin, and antihistaminic agents.

Cyroheptadine and several derivatives are known tricyclic compounds with antiserotonin and antihistamine activity as described in U.S. Pat. No. 3,014,911. It is also known that the cyano- and trifluoromethylthio-derivatives of cyproheptadine, as described in U.S. Pat. Nos. 3,988,342 and 4,031,222 are antipsychotic agents.

Now with this invention there are provided related hetero-tricyclic compounds with somewhat analogous utilities. Accordingly, it is an object of this invention to provide certain pyrrolo [2,1-b] [3]benzazepines with a piperidinylidene group in the 11-position and non-toxic pharmaceutically acceptable salts thereof. Another object is to provide a method of treating psychoses, and disease states with which are associated abnormally high levels of serotonin and/or histamine, activity with the novel compounds. Another object is to provide pharmaceutical formulations comprising the novel compounds. A fourth object is to provide novel processes for the synthesis of the novel compounds.

DETAILED DESCRIPTION OF THE INVENTION

The compounds of the present invention have the following structural formula:

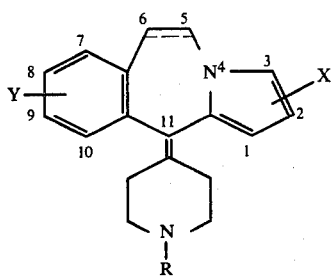

I or pharmaceutically acceptable salt thereof, wherein the dotted line represents saturation or unsaturation; X and Y are independently
 (1) hydrogen,
 (2) halogen such as chloro, bromo, fluoro, or iodo,
 (3) trifluoromethyl,
 (4) lower alkyl, especially $C_{1-4}$ alkyl, or
 (5) lower alkoxy, especially $C_{1-4}$ alkoxy,
 (6) cyano,
 (7) trifluoromethylthio, or
 (8) trifluoromethylsulfonyl;
and R is
 (1) lower alkyl, especially $C_{1-4}$ alkyl, or
 (2) cyclopropylmethyl.

A preferred embodiment of the novel compounds of this invention is the compound of structural formula:

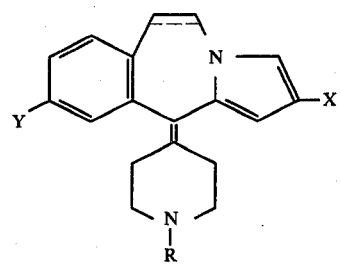

Ia or pharmaceutically acceptable salt thereof, wherein X, Y, and R are as defined above.

A still more preferred embodiment is where one of X and Y is hydrogen, and the other is hydrogen, chloro, cyano, or trifluoromethylthio.

Also contemplated to be within the scope of the present invention are pharmaceutically acceptable acid addition salts. These salts, prepared by conventional means, include the hydrochloride, maleate, sulfate, phosphate, citrate, tartrate, succinate, and the like.

The novel processes of this invention comprise treatment of a pyrrolobenzazepin-11-one, II, with a 1-R-piperidin-4-ylmagnesium chloride, followed by dehydration of the resulting carbinol compound, III, to the final product, I, as illustrated below:

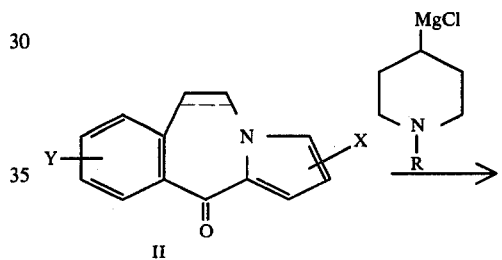

II

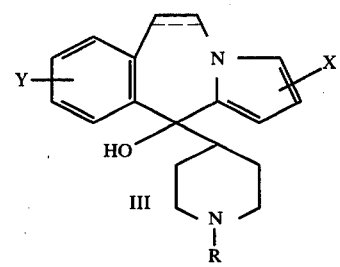

III

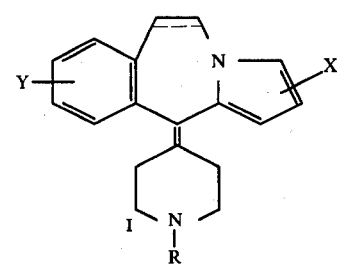

I

The ketone starting material (II) is treated with the Grignard reagent in a solvent such as tetrahydrofuran, ether, or the like at a temperature of from about $-10°$ C. to reflux for from about 10 minutes to about 10 hours to provide the 11-hydroxy intermediate, (III), which species is then dehydrated by treatment with an acid such as hydrochloric, oxalic, trifluoroacetic, formic, acetic, trifluoroacetic anhydride, trichloroacetic acid, phosphorous oxychloride with a tertiary amine, or the like at a temperature of from about 0 to about 100° C. for from about 5 minutes to about 24 hours to provide the final product pyrrolobenzazepines. The Grignard reaction and the subsequent dehydration described above are substantially identical to those disclosed in U.S. Pat. Nos. 3,014,911 (issued Dec. 26, 1961), 2,951,082 (issued Aug. 30, 1960), 3,428,677 (issued Feb. 18, 1969), 3,428,735 (issued Feb. 18, 1969), 3,454,643 (issued July 8, 1969), and 3,499,037 (issued Mar. 3, 1970), all to Edward L. Engelhardt or Edward L. Engelhardt et al.

The important intermediate 11-hydroxy compounds of Structure III form another embodiment of this invention wherein the symbols X, Y, and R, are as previously defined for the compounds of Structure I.

The novel compounds of this invention of structure I or a pharmaceutically acceptable salt thereof, possess antipsychotic, antiserotonin and antihistaminic activity and may be administered to patients requiring antipsychotic, antiserotonin and/or antihistamine treatment in any of the usual pharmaceutical forms such as powders, capsules, tablets, elixirs, and aqueous suspension, in the amount of from about 1 to about 750 mgms per day, preferably in divided doses taken 2 to 4 times daily. Sterile solutions for injection purposes would be administered in amounts of from 0.1 to 150 mgms per day.

The following examples illustrate the novel processes of this invention used for the synthesis of the novel carbinol intermediates and products of this invention and are not meant to limit the invention to the particular process conditions used and products produced thereby.

EXAMPLE 1

1-Methyl-4-[6,11-dihydro-5H-pyrrolo[2,1-b] [3]benzazepin-11-ylidene]piperidine

Step A: Preparation of 11-hydroxy-11-(1-methyl-piperidin-4-yl)-6,11-dihydro-5H-pyrrolo[2,1-b] [3]benzazepine 6,11-Dihydro-5H-pyrrolo[2,1-b] [3]benzazepin-11-one (7 g., 35.6 mmol) is dissolved in 100 ml. of tetrahydrofuran and to it is added with stirring 200 ml. of tetrahydrofuran containing 0.425 mmoles/ml. of 1-methyl-piperidin-4-ylmagnesium chloride. After a few minutes of stirring, 40 ml. of water is added and after another few minutes the mixture is diluted with methylene chloride. The organic phase is separated, dried over magnesium sulfate, filtered, and concentrated to dryness. The residue is chromatographed on a silica gel column (1.5 × 17 inches) by elution with 5% (v/v) methanol in chloroform. Combination of the appropriate fractions and evaporation to dryness gives 7.3 g. of 11-hydroxy-11-(1-methyl-piperidin-4-yl)-6,11-dihydro-5H-pyrrolo[2,1-b] [3]benzazepine, m.p. 175-177° C.

Step B: Preparation of 1-methyl-4-[6,11-dihydro-5H-pyrrolo-[2,1-b] [3]benzazepin-11-ylidene]piperidine The hydroxy compound from Step A (3.02 g., 10.2 mmole) and 950 mg. of oxalic acid in 100 ml. of absolute ethanol is refluxed 2 hours. Oxalic acid (50 mg.) is added and refluxing is continued for 15 minutes. Oxalic acid 100 mg. is added and refluxing is continued for ½ hour. The mixture is cooled to room temperature, then in an icebath and finally in a freezer overnight. The precipitate is collected, washed with ethanol, and dried under nitrogen to give 2.78 g. of the oxalic acid salt of 1-methyl-4-[6,11-dihydro-5H-pyrrolo-[2,1-b] [3]benzazepin-11-ylidene]piperidine, m.p. 239° C. (decomp.)

Following the procedure of Example I, Step B, there may be substituted for the oxalic acid in ethanol dehydration system (1) used therein, trifluoroacetic anhydride-chloroform (2), trifluoroacetic acid (3), hydrogen chloride in chloroform (4), phosphorus oxychloride-pyridine (5), trichloroacetic acid-ethanol (6), acetic acid (7), or formic acid (8).

Employing the procedure substantially as described in Example 1, Steps A and B, but substituting for the 6,11-dihydro-5H-pyrrolo[2,1-b] [3]benzazepin-11-one and 1-methyl-piperidin-4-yl magnesium chloride used in Step A, the substituted ketones and 1-R-piperidin-4-yl magnesium chlorides described in Tables I and II in the same relative molecular amounts, there are produced the respective 11-hydroxy-11-piperidin-4-yl and 11-piperidinylidene compounds also described in Tables I and II, by the previously described novel process.

Table I

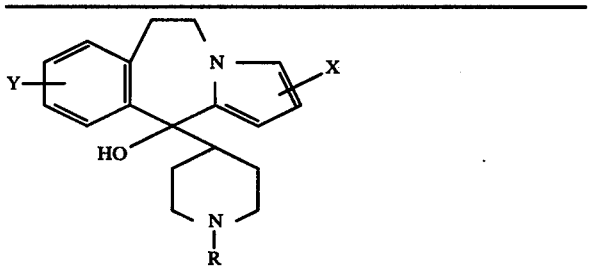

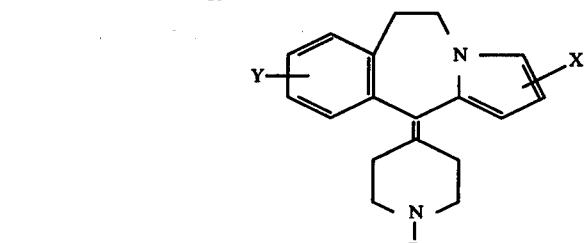

| R | Y | X | Dehydration* System | m.p. (° C.) |
|---|---|---|---|---|
| CH₃ | H | 2-SO₂CF₃ | 4 | |
| CH₃ | H | 2-CN | 2 | 208–209(dec)ᵃ |
| CH₃ | H | 2-CF₃ | 4 | |
| CH₃ | H | 2-Br | 4 | |
| CH₃ | H | 2-Cl | 4 | 221–222(dec)ᵃ |
| CH₃ | H | 2-SCF₃ | 4 | 101–102 |
| CH₃ | 9-OCH₃ | 2-CN | 2 | |
| CH₃ | 9-CH₃ | H | 1 | |
| CH₃ | 9-CH(CH₃)₂ | H | 1 | |
| CH₃ | H | 2-CH₃ | 1 | |
| CH₃ | 9-I | H | 4 | |
| CH₃ | 9-Cl | H | 4 | |
| CH₃ | 9-SCF₃ | H | 4 | 138–139 |
| CH₃ | 9-CN | H | 4 | 177–179 |
| CH₃ | 9-SO₂CF₃ | H | 4 | |
| —CH₂◁ | H | 2-SO₂CF₃ | 4 | |
| —CH₂◁ | H | 2-SCF₃ | 4 | |
| —CH₂◁ | H | 2-Cl | 4 | |
| —CH₂◁ | 9-SO₂CF₃ | H | 4 | |
| —CH₂◁ | 9-SCF₃ | H | 4 | |
| —CH₂◁ | 9-Cl | H | 4 | |

*See paragraph following Example 1, Step B
ᵃoxalate salt

Table II

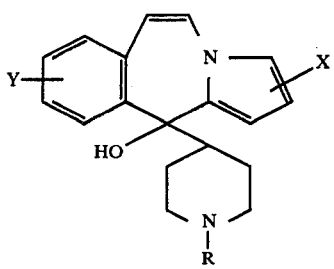

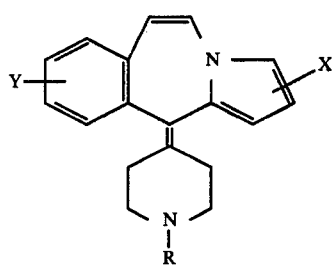

| R | Y | X | Dehydration* System | m.p. (° C.) |
|---|---|---|---|---|
| CH₃ | H | 2-CN | 2 | 217-219(dec)[a] |
| CH₃ | H | 2-SCF | 4 | 120-121 |
| CH₃ | 9-Cl | H | 4 | |
| CH₃ | 9-SCF₃ | H | 4 | 124-126 |
| CH₃ | 9-CN | H | 1 | 158-161 |
| CH₃ | H | 2-Cl | 4 | |
| CH₃ | 9-Br | H | 4 | 138-142 |
| CH₃ | 9-I | H | 4 | |
| CH₃ | 9-OCH₃ | H | 4 | |
| CH₃ | H | 3-CF₃ | 4 | |
| CH₃ | H | 2-SO₂CF₃ | 4 | |
| CH₃ | H | H | 4 | |
| —CH₂◁ | H | 2-SCF₃ | 4 | |
| —CH₂◁ | H | 2-Cl | 4 | |
| —CH₂◁ | H | 2-SO₂CF₃ | 4 | |
| —CH₂◁ | 9-SCF₃ | H | 4 | |
| —CH₂◁ | 9-Cl | H | 4 | |

*See paragraph following Example 1, Step B
[a]oxalate salt

EXAMPLE 2

1-Methyl-4-[9-cyano-11H-pyrrolo[2,1-b] [3]benzazepin-11-ylidene]piperidine

1-Methyl-4-[9-bromo-11H-pyrrolo[2,1-b] [3]benzazepin-11-ylidene]piperidine (6.3 g., 0.017 mole) and cuprous cyanide (3.2 g., 0.035 mole) in 25 ml. of dry dimethylformamide are refluxed under nitrogen for five hours. The mixture is cooled to an internal temperature of 50° and treated with 60 ml. each of benzene and aqueous saturated sodium cyanide solution. After stirring one hour the contents are transferred to a separatory funnel with the aid of additional benzene and water. The aqueous phase is extracted two times with benzene, once with ether and the combined benzene-ether extracts are washed successively with dilute sodium cyanide, water, dilute ammonium hydroxide, and water. Upon drying over sodium sulfate the solvents are evaporated in vacuo to give 1-methyl-4-[9-cyano-11H-pyrrolo[2,1-b] [3]benzazepin-11-ylidene]piperidine as an oil (5.0 g., 94%). Trituration with acetonitrile gives a solid (3.6 g., m.p. 156-159° C.). An analytical sample is obtained after one recrystallization from acetonitrile, m.p. 158-161° C.

EXAMPLE 3

Pharmaceutical Compositions

A typical tablet containing 10 mg. 1-methyl-4-[9-cyano-11H-pyrrolo[2,1-b] [3]benzazepin-11-ylidene]piperidine per tablet is prepared by mixing together with the active ingredient calcium phosphate, lactose and starch in the amounts shown in the tables below. After these ingredients are thoroughly mixed, the dry mixture is blended for an additional three minutes. This mixture is then compressed into tablets weighing approximately 134 mg. each. Similarly prepared are tablets containing 1-methyl-4-[11H-pyrrolo-[2,1-b] [3]benzazepin-11-ylidene]piperidine, 1-methyl-4-[6,11-dihydro-2-methoxy-5H-pyrrolo [2,1-b] [3]-benzazepin-11-ylidene]piperidine, or any of the novel compounds of this invention of Structure I.

| Tablet Formula | |
|---|---|
| Ingredient | Mg. per Tablet |
| 1-methyl-4-[9-cyano-11H-pyrrolo-[2,1-b][3]benzazepin-11-ylidene]piperidine | 10 mg. |
| Calcium phosphate | 52 mg. |
| Lactose | 60 mg. |
| Starch | 10 mg. |
| Magnesium stearate | 1 mg. |

What is claimed is:
1. A compound of structural formula:

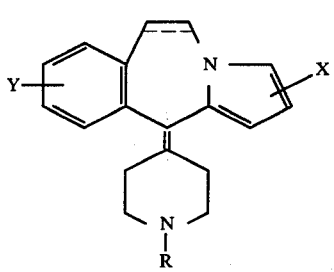

or a pharmaceutically acceptable salt thereof, wherein X and Y are independently hydrogen, halogen, trifluoromethyl, lower alkyl, lower alkoxy, cyano, trifluoromethylthio, or trifluoromethylsulfonyl; and R is lower alkyl or cyclopropylmethyl.

2. The compound of claim 1 with structural formula:

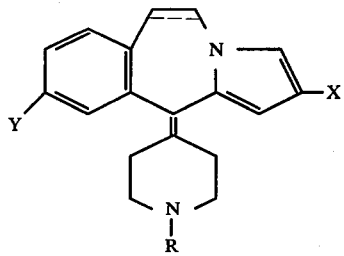

or a pharmaceutically acceptable salt thereof, wherein X, Y and R are as defined in claim 1.

3. The compound of claim 2 or a pharmaceutically acceptance salt thereof, wherein one of X and Y is hydrogen, and the other is hydrogen, chloro, cyano or trifluoromethylthio.

4. A compound of structural formula:

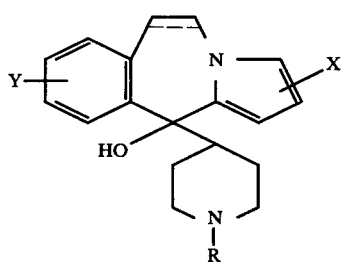

wherein X and Y are independently hydrogen, halogen, trifluoromethyl, lower alkyl, lower alkoxy, cyano, trifluoromethylthio, or trifluoromethylsulfonyl; and R is lower alkyl or cyclopropylmethyl.

5. The compound of claim 4 with structural formula:

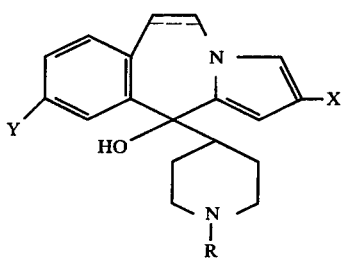

wherein X, Y and R are as defined in claim 4.

6. The compound of claim 5, wherein one of X and Y is hydrogen, and the other is hydrogen, chloro, cyano or trifluoromethylthio.

7. A pharmaceutical composition for the treatment of psychoses or a disease state associated with abnormally high levels of serotonin or histamine comprising a pharmaceutical carrier and an effective antipsychotic, antiserotonin, or antihistamine amount respectively of a compound of structural formula:

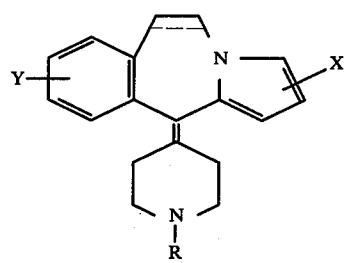

or a pharmaceutically acceptable salt thereof, wherein X and Y are independently hydrogen, halogen, trifluoromethyl, lower alkyl, lower alkoxy, cyano, trifluoromethylthio, or trifluoromethylsulfonyl; and R is lower alkyl or cyclopropylmethyl.

8. The pharmaceutical composition of claim 7 wherein the compound has structural formula:

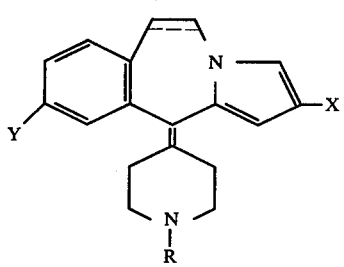

or a pharmaceutically acceptable salt thereof, wherein X, Y and R are as defined in claim 7.

9. The pharmaceutical composition of claim 8 wherein in the compound or a pharmaceutically acceptable salt thereof, one of X and Y is hydrogen and the other is hydrogen, chloro, cyano or trifluoromethylthio.

10. A method of treating psychoses or disease states associated with abnormally high levels of serotonin or histamine activity which comprises the administration to a patient in need of such treatment an effective antipsychotic, antiserotonin, or antihistamine amount respectively of a compound of structural formula:

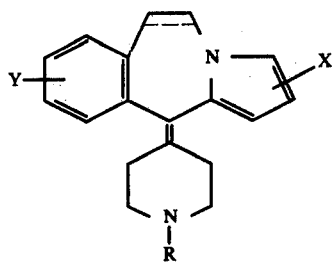

or a pharmaceutically acceptable salt thereof, wherein X and Y are independently hydrogen, halogen, trifluoromethyl, lower alkyl, lower alkoxy, cyano, trifluoromethylthio, or trifluoromethylsulfonyl; and R is lower alkyl or cyclopropylmethyl.

11. The method of claim 10, wherein the compound has structural formula:

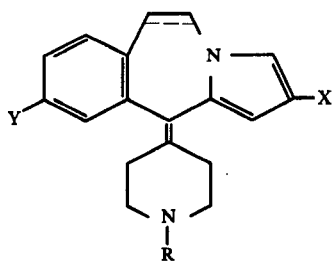

or a pharmaceutically acceptable salt thereof, wherein X, Y and R are as defined in claim 10.

12. The method of claim 11, wherein in the compound or a pharmaceutically acceptable salt thereof, one of X and Y is hydrogen and the other is hydrogen, chloro, cyano, or trifluoromethylthio.

* * * * *